(12) United States Patent
Xu et al.

(10) Patent No.: US 6,419,906 B1
(45) Date of Patent: Jul. 16, 2002

(54) STRIP FOR WHITENING TOOTH SURFACES

(75) Inventors: Guofeng Xu, Princeton; David B. Viscio, Monmouth Junction, both of NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/804,530

(22) Filed: Mar. 12, 2001

(51) Int. Cl.[7] .............................. A61K 7/16; A61K 7/20
(52) U.S. Cl. ...................... 424/53; 424/401; 424/435
(58) Field of Search ...................... 424/401, 53, 435

(56) References Cited

U.S. PATENT DOCUMENTS

| | | | | |
|---|---|---|---|---|
| 4,713,243 A | * | 12/1987 | Schiraldi, I et al. | 424/435 |
| 4,795,584 A | * | 1/1989 | Russ et al. | 252/174.23 |
| RE33,093 E | * | 10/1989 | Schiraldi, II et al. | 424/435 |
| 5,480,577 A | * | 1/1996 | Nicholson et al. | 252/174.13 |
| 5,851,551 A | * | 12/1998 | Tseng et al. | 424/435 |
| 5,879,691 A | * | 3/1999 | Sagel, I et al. | 424/401 |
| 5,891,453 A | * | 4/1999 | Sagel, III et al. | 424/401 |
| 5,894,017 A | * | 4/1999 | Sagel, II et al. | 424/401 |
| 6,045,453 A | * | 4/2000 | Dirksing et al. | 424/401 |
| 6,096,328 A | * | 8/2000 | Sagel, IV et al. | 424/401 |
| 6,136,297 A | * | 10/2000 | Sagel, V et al. | 424/401 |

* cited by examiner

Primary Examiner—Shep K. Rose
(74) Attorney, Agent, or Firm—Paul Shapiro; Richard E. Nanfeldt

(57) ABSTRACT

A thin, flexible film which when applied to stained teeth is hydrated by saliva and is effective in such form to whiten teeth, the film comprising an anhydrous water hydratable ethylene oxide polymer matrix containing a solid peroxide whitening agent whereby upon application to stained tooth surfaces, the peroxide whitening agent is solublilized by saliva present in the oral cavity into active whitening activity when the film is positioned and placed on the teeth.

12 Claims, No Drawings

STRIP FOR WHITENING TOOTH SURFACES

FIELD OF THE INVENTION

This invention relates generally to a system for whitening human teeth, and more particularly to a strip for applying a whitening agent to teeth in order to remove stains from the surface thereof.

BACKGROUND OF THE INVENTION

The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a film over the teeth. These staining and discoloring substances can then permeate the enamel layer. This problem occurs gradually over many years, but imparts a noticeable discoloration of the enamel of one's teeth.

Means known to the art to effect whitening of teeth include the application, as by brushing, to the teeth of peroxide containing dentifrice compositions of the type disclosed in U.S. Pat. Nos. 5,256,402 and 5,814,309.

More recently a variety of over-the-counter tooth whitening systems have become available, including a whitening system comprised of a thin strip of plastic film having applied to a surface thereof a tooth whitening composition as described in U.S. Pat. Nos. 5,894,017, 5,891,453 and 6,045, 811. Although these systems produce a whitening effect when applied to stained teeth, the art is continually seeking new systems to improve and heighten tooth whitening.

SUMMARY OF THE INVENTION

According to the present invention there is provided a system for applying a composition containing agents to whiten the stained surface of the teeth wherein there is provided a thin film capable of adhering to moist tooth surfaces comprising a dried, water hydratable matrix comprised of one or more polymers of ethylene oxide, and a water soluble plasticizer, the matrix having incorporated therein a solid water soluble whitening agent in an amount effective, when solubilized by saliva in the oral cavity to be released from the film, to whiten the teeth to which the film is applied.

DESCRIPTION OF THE PREFERRED EMBODIMENTS

The water hydratable poly(ethylene) oxide films of the present invention can be made in thickness of about 20 to about 1500 micrometer ($\mu$m) and preferably about 50 to about 1000 $\mu$m The dried film contains the solid peroxide whitening agent in an inactive state. Hydration of the film by saliva in the oral cavity solubilizes the water soluble solid whitening agent incorporated in the ethylene oxide polymer matrix whereby the whitening agent is activated and released to the tooth surfaces to which the film is applied.

The rate at which the whitening agent is solubilized and thereafter released into contact with tooth surfaces is controlled by varying the film thickness, polymer properties, as well as the whitening agent concentration, such concentration generally varying from about 0.1 to about 30% by weight and preferably about 0.5 to about 25% by weight of the film.

The solid whitening agents suitable for the practice of the present invention include peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite. The preferred chlorite is sodium chlorite. A preferred percarbonate is sodium percarbonate. Preferred persulfates are oxones.

Ethylene oxide polymers useful for purposes of the present invention include homopolymers or mixtures of ethylene oxide polymers of varying molecular weight ranging from about 10,000 Daltons and up to about 10,000,000 Daltons and preferably in the range of about 100,000 to about 1,500,000 Daltons. Such ethylene oxide polymers are commercially available from various sources. Poly (ethylene) oxide in the molecular weight range of 10,000 to 1,000,000 Daltons is available from the Union Carbide Company under the tradename "Polyox" and are preferred for purposes of the present invention. The ethylene oxide polymer comprises about 50 to about 95% by weight of the film of the present invention and preferably about 60 to about 85% by weight.

The plasticizer useful for purposes of the present invention are selected from glycols such as propylene glycol, polyethylene glycol, polyhydric alcohols such as glycerin and sorbitol and glycerol esters such as glycerol triacetate. The plasticizer comprises about 5 to about 30% by weight of the film of the present invention and preferably about 10 to about 25% by weight.

Glycerin is the preferred plasticizer for use in the present invention as well as propylene glycol or polyethylene glycol such as is available from Union Carbide Corporation as their series of Carbowaxes which range in molecular weight from 200 to 600 Daltons.

In addition to the incorporation of peroxide whitening agents and plasticizer there may also be included in the film matrix minor amounts, e.g., 0.01 to 2% by weight of ingredients such as antioxidants, preservatives, flavors and colorants.

One side of the ethylene oxide polymer film can be also coated with a thin protective coating layer, e.g., of 10 nanometers (nm) to 500 microns (um) thickness which serves as a barrier to prevent release of the solublized whitening agent from the matrix to the oral mucosa, thereby achieving unidirectional release of the whitening agent solely on the tooth surfaces.

The coating material is applied in a sufficiently thin layer so as not to interfere with the flexibility of the film and to allow the whitening strip to conform to an arrangement of a row of teeth.

The coating materials can be one or a combination of high molecular weight (that is, molecular weights greater than 1,000,000 Dalton) and include, ethyl cellulose, propyl cellulose, isopropyl cellulose, butyl cellulose, t-butyl cellulose, cellulose acetate, and derivatives of polyvinyl alcohol such as polyvinyl acetate and shellac.

The ethylene oxide polymer film of the present invention can be prepared using conventional extrusion or solvent casting processes. For example, to prepare a film by solvent casting poly(ethylene) oxide, the ethylene oxide polymer or mixture of polymers is dissolved in a sufficient amount of a solvent which is compatible with the polymer. Examples of suitable solvents include water, alcohols, acetone, ethyl acetate or mixtures thereof. After a solution has been formed, a plasticizer is added with stirring, and heat is applied if necessary to aid dissolution, until a clear and homogeneous solution has been formed, followed by the addition of the whitening agent and any other ingredients such as flavors. The solution is coated onto a suitable carrier material and dried to form a film. The carrier material must have a surface tension which allows the polymer solution to spread evenly across the intended carrier width without soaking in to form a destructive bond between the two substrates. Examples of suitable carrier materials include glass, stainless steel, teflon, polyethylene-impregnated kraft paper.

Drying of the film may be carried out in a high-temperature air-bath using a drying oven, drying tunnel, vacuum drier, or any other suitable drying equipment, which does not adversely affect the active ingredient(s) or flavor of the film.

For ease of use, the dry film is cut into pieces of suitable size and shape and packed into a suitable container.

To use the whitening film strip of the present invention, the film when applied to the teeth surface when hydrated by saliva in the oral cavity or prewetted by dipping the strip in water will adhere to the teeth in an appropriate manner. In this regard, the whitening strip is formed to have a width dimension suitable to cover a row of teeth (upper or lower). Therefore, the whitening strip may be applied to the upper set of teeth, or to the lower set of teeth either separately or simultaneously. The length dimension of the whitening strip is determined by the amount of coverage desired. In this regard, the number of teeth which it is desired to whiten will determine the dimensions of the whitening strip. For instance, it may be desired to only whiten the front teeth, which are most easily seen by others. Accordingly, the length of whitening strip can be reduced in this case, as compared to the case where it is desired to whiten all of the teeth. The duration of application of whitening strip to the teeth will depend upon the type and concentration of the whitening agent, as well as the type and intensity of stain. The present invention is illustrated by the following examples.

EXAMPLE 1

10.0 grams (g.) of polyethylene oxide (M.W. 200,000, Aldrich) was slowly added into about 85.0 g., deionized water heated to about 80° C., with vigorous stirring to form a translucent and viscous solution. To this solution was added, 2.5 g. glycerin and stirred for about 30 minutes. The mixture was cooled down to below 40° C. and 2.4 g. sodium percarbonate powder was added and thoroughly mixed. The resulting white mixture was cast onto a glass plate and allowed to dry overnight. A white dry film was formed which was readily peeled off from the glass plate. The dry film had a thickness of about 160 µm and contained an equivalent of about 3.4% hydrogen peroxide by weight of the film.

The whitening efficacy of this film (designated "Film A") was examined by wetting and placing piece of the film (14 mm×15 mm, weighing 23 milligrams (mg.) against the surface of a stained bovine enamel slab prepared as described in "In Vitro Removal of Stain with Dentifrice", G. K. Stookey, T. A. Barkhard and B. R. Schemerhorn, J. Dental Res., 61, 1236–9 (1982) and obtained from Oral Health Research Institute of Indiana University. A piece of wet paper towel was placed on top of the film to maintain the moisture. After 30 minutes, both the towel and the residue film were removed and the tooth was washed with water. The shade of the tooth was measured and recorded both before and after the treatment with a Minolta Chromometer Model CR 321 in which "L" is a measure of response to the eye to lightness and darkness, the higher the L value the whiter teeth appear.

For purposes of comparison, a commercially available tooth whitening strip of the type disclosed in U.S. Pat No. 5,894,017 containing 5.2% by weight hydrogen peroxide (designated "Film B") was also cut into a similar dimension which weighed 40 mg was used to treat a similarly stained bovine enamel slab for 30 minutes following the procedure of Example 1. The change in L values of the treated Films A and B are recorded in Table I below.

TABLE I

| Film | Weight (mg) | H$_2$O$_2$ wt. % | Initial L | End L | dL |
| --- | --- | --- | --- | --- | --- |
| A | 23 | 3.4 | 37.32 | 62.09 | 24.77 |
| B | 40 | 5.2 | 37.43 | 44.67 | 7.24 |

The results recorded in Table I above show that the whitening efficacy of Film A prepared in accordance with the present invention is unexpectedly much higher than that of commercial white strip (Film B), despite having a significantly lower peroxide content

EXAMPLE 2

A series of films was prepared using 1.0 g poly(ethylene) oxide (M.W. 400,000 Daltons) which was slowly added with vigorous stirring into about 80.0 g hot deionized water heated to about 80° C. While maintaining the same temperature and continuing agitating, another 10.0 g poly (ethylene) oxide (M. W. 200,000 Daltons) was slowly added into the solution. After the complete dissolution of the polyethylene oxide, a translucent and viscous solution/suspension was formed. The solution was concentrated by heating and stirring at about 80° C. for another two hours. The solution was then cooled to room temperature (23° C).

To the above solution, 3.3 g. glycerin was added and stirred for about 30 minutes, until a homogeneous solution was obtained. Subsequently, 3.0 g sodium percarbonate powder was added and thoroughly mixed with the poly (ethylene) oxide solution to form a white, thick gel-like suspension.

A free-standing film was prepared by casting the above gel-like suspension onto glass plates and drying at room temperature (23° C.) overnight. After drying, a film was formed and could be readily peeled off from the glass plates. The film was flexible and strong and could be bent or folded without breaking. Both thin and thick films were prepared. A thin film designated "C" had a thickness of about 100 um and contained about 2.9% hydrogen peroxide by weight.

A thicker film designated "Film D" had a thickness of 500 um and a hydrogen peroxide content of 3.4% by weight.

A third supported film was prepared by casting the poly(ethylene) oxide suspension prepared as above onto a flexible cotton cloth and dried in air. The resulting strip (designated "Film E") had a hydrogen peroxide content of 1.5% by weight by weight of the supported film.

The whitening test procedure of Example I using stained bovine enamel slabs was repeated to determine the tooth-whitening efficacy of Films C, D and E. The shade change of the tooth was recorded using the Minolta Chromometer Model CR 321 both before and after the treatment. As a comparison, a piece of a commercially available whitening strip (Film B of Example I) was also cut into a similar dimension and used to treat another bovine tooth for 30 minutes. The results of these tests are recorded in Table II.

TABLE II

| Film | $H_2O_2$ wt. % | Initial L | End L | dL |
| --- | --- | --- | --- | --- |
| C | 2.9 | 28.98 | 47.56 | 18.58 |
| D | 3.4 | 38.28 | 65.21 | 26.93 |
| E | 3.0 | 40.07 | 61.82 | 21.75 |
| B | 4.6 | 33.33 | 41.54 | 8.21 |

The shade of the stained bovine enamels slabs after the 30 minute exposure to the Films C, D and E of the present invention showed superior whitening efficacy as compared to the comparative commercial whitening strip Film B.

What is claimed is:

1. A strip for whitening teeth in order to remove stains from the surface of said teeth, wherein said strip comprises approximately by weight:
   (a) 50% to 90% of a matrix consisting of an anhydrous water hydratable ethylene oxide polymer; and
   (b) 1% to 30% of a solid whitening agent being incorporated in said matrix, wherein upon application of said strip to said teeth said solid whitening agent is solubilized by saliva present in the oral cavity into active whitening activity when said strip is positioned and place on said teeth.

2. The strip of claim 1 wherein the ethylene oxide polymer has a molecular weight of a range of about 100,000 to 10,000,000 Daltons.

3. The strip of claim 1 wherein the ethylene oxide polymer has a molecular weight range of about 100,000 to about 1,500,000 Daltons.

4. The strip of claim 1 wherein the whitening agent is sodium percarbonate.

5. The strip of claim 1 wherein a plasticizer is incorporated in the matrix.

6. The strip of claim 1 wherein the plasticizer is present in the matrix at a concentration of about 5.0 to about 30.0% by weight.

7. The strip of claim 5 wherein the plasticizer is glycerin.

8. The strip of claim 1 having a thickness in the range of about 20 to about 1500 μm.

9. The strip of claim 1 wherein said whitening agent is selected from the group consisting of peroxides, metal chlorites, perborates, percarbonates, peroxyacids and persulfates and mixtures thereof.

10. The strip of claim 1 further including a plasticizer incorporated at a concentration level of 5 wt. % to 30 wt. % in said matrix, wherein said plasticizer is selected from the group consisting of glycols, polyhydric alcohols and glycerol esters.

11. The strip of claim 9 further including a plasticizer incorporated at a concentration level of 5 wt. % to 30 wt. % in said matrix, wherein said plasticizer is selected from the group consisting of glycols, polyhydric alcohols and glycerol esters.

12. The strip of claim 1 further including a coating material adhered to a surface of said matrix, said coating material being selected from the group consisting of ethyl cellulose, propyl cellulose, isopropyl cellulose, butyl cellulose, t-butyl cellulose, cellulose acetate, polyvinyl acetate and shellac.

* * * * *